(12) United States Patent
Takaoka et al.

(10) Patent No.: US 9,131,714 B2
(45) Date of Patent: Sep. 15, 2015

(54) OIL-ADSORBING COMPOSITION, METHOD FOR ITS PRODUCTION, AND METHOD FOR USING THE OIL-ADSORBING COMPOSITION

(75) Inventors: Seizo Takaoka, Itami (JP); Yasutoshi Hishikawa, Itami (JP); Hiroyuki Kataoka, Itami (JP)

(73) Assignee: MATSUTANI CHEMICAL INDUSTRY CO., LTD., Itami (JP)

( * ) Notice: Subject to any disclaimer, the term of this patent is extended or adjusted under 35 U.S.C. 154(b) by 552 days.

(21) Appl. No.: 13/252,431

(22) Filed: Oct. 4, 2011

(65) Prior Publication Data

US 2012/0088849 A1    Apr. 12, 2012

(30) Foreign Application Priority Data

Oct. 8, 2010   (JP) ................. 2010-229029

(51) Int. Cl.
*A61K 47/36* (2006.01)
*A23L 1/09* (2006.01)
*B01J 20/26* (2006.01)
*B01J 20/28* (2006.01)

(52) U.S. Cl.
CPC ............. *A23L 1/095* (2013.01); *B01J 20/262* (2013.01); *B01J 20/28011* (2013.01); *B01J 20/28021* (2013.01); *A61K 47/36* (2013.01)

(58) Field of Classification Search
None
See application file for complete search history.

(56) References Cited

U.S. PATENT DOCUMENTS

| 2,797,201 A | 6/1957 | Veatch et al. |
| 2005/0131143 A1* | 6/2005 | Ugazio ........................... 525/71 |

FOREIGN PATENT DOCUMENTS

| EP | 0659403 A2 | 6/1995 |
| EP | 0659403 B1 | 6/1995 |
| EP | 0659403 A3 | 7/1996 |
| JP | 53-23305 | 3/1978 |
| JP | A-53-23305 | * 3/1978 |
| JP | 07223973 A | 8/1995 |

* cited by examiner

*Primary Examiner* — Melvin C Mayes
*Assistant Examiner* — Colette Nguyen
(74) *Attorney, Agent, or Firm* — Kratz, Quintos & Hanson, LLP

(57) ABSTRACT

Conventional dried materials have a low oil adsorption property and oil retention ability. Therefore, a dried material that has an excellent oil adsorbing property and oil retention ability has been desired. Accordingly, an object of the present invention is to provide an oil-adsorbing composition that has an excellent oil adsorption property and oil retention ability; a method for producing the oil-adsorbing composition; and a method for using the oil-adsorbing composition.

8 Claims, 2 Drawing Sheets

US 9,131,714 B2

OIL-ADSORBING COMPOSITION, METHOD FOR ITS PRODUCTION, AND METHOD FOR USING THE OIL-ADSORBING COMPOSITION

TECHNICAL FIELD

The present invention relates to an oil-adsorbing composition that has an oil adsorption property or oil retention ability and that can easily convert oil into a powder; a method for producing the oil-adsorbing composition; and a method for using the oil-adsorbing composition.

BACKGROUND ART

Conventional oil-adsorbing compositions are generally in the form of a porous film or a granular material derived therefrom. When such an oil-adsorbing composition having an oily substance adsorbed thereon is mixed with various types of solvents, the composition releases the oily substance retained. In particular, when such an oil-adsorbing composition is mixed with water, the oily substance once adsorbed on the composition is readily released therefrom. Oil-adsorbing compositions that have the property of adsorbing an oily substance thereon or retaining an oily substance therein and then releasing the adsorbed oily substance in a solvent such as water can find a wide range of applications. Accordingly, its industrial use has been contemplated in various fields.

As a starting material component for the oil-adsorbing composition, a starch-derived substance has been attracting attention. This is because a starch-derived substance can find a wide variety of applications due to ease of processing, and no environmental damage caused by its incineration after oil adsorption. Conventionally, an oil-adsorbing composition having an oil adsorption property and oil retention ability is produced by a method comprising pouring an aqueous solution of a starch hydrolysate or a reduced starch hydrolysate between roll slits (drums) of a drum dryer; then boiling and drying the solution to form a porous film, and crushing and powdering the porous film (Patent Literature 1).

Patent Literature (PTL) 1 discloses that the oil-adsorbing composition thus obtained is highly soluble in water, and can smoothly release an oily substance when placed into water.

CITATION LIST

Patent Literature

PTL 1: Japanese Unexamined Patent Publication No. S53-23305

SUMMARY OF INVENTION

Technical Problem

As described above, in the conventional technique, an oil-adsorbing composition is produced by boiling and drying a solution of a starch hydrolysate disposed between roll slits of a drum dryer; and crushing a dried material, such as a porous film, obtained by the boiling and drying step.

However, the oil-adsorbing composition thus produced is insufficient in terms of oil adsorption property and oil retention ability, and further improvement has been required. An oil-adsorbing composition having an excellent oil adsorption property and oil retention ability, and a production method thereof comprising simplified steps have been desired.

Accordingly, an object of the present invention is to provide an oil-adsorbing composition having an excellent oil adsorption property and oil retention ability; a method for producing the oil-adsorbing composition; and a method for using the oil-adsorbing composition.

Solution to Problem

As a result of repeated extensive research to achieve the above object, the present inventors found that when hollow spheres are prepared by a method comprising spraying a solution containing at least one member selected from the group consisting of starch hydrolysates and reduced starch hydrolysates onto a drying surface, drying the solution in a droplet form, and exfoliating the resulting dried material, a composition containing such hollow spheres and fragments thereof has an excellent oil adsorption property and oil retention ability, compared to the oil-adsorbing composition produced by the aforementioned conventional method. The inventors further found that the above composition can be produced by a method comprising simplified production steps, thus enabling mass production. The present invention has been accomplished based on the above finding.

(I) Oil-Adsorbing Composition

Item 1. An oil-adsorbing composition comprising hollow spheres, the hollow spheres being obtained by drying a solution containing at least one member selected from the group consisting of starch hydrolysates and reduced starch hydrolysates in a droplet form, and exfoliating the resulting dried material.

Item 2. An oil-absorbing composition according to claim 1 which comprising hollow spheres and fragments thereof.

Item 3. An oil-adsorbing composition according to Item 1 which has a bulk specific gravity of 6 $cm^3/g$ or more.

(II) Method for Producing an Oil-Adsorbing Composition

Item 4. A method for producing an oil-adsorbing composition by drying a solution containing at least one member selected from the group consisting of starch hydrolysates and reduced starch hydrolysates, the method comprising the steps of:

(a) spraying the solution onto a drying surface and drying the solution in a droplet form; and (b) exfoliating the dried material obtained in step (a).

The dried material is exfoliated with, for example, a scraper knife, while maintaining the droplet form.

Item 5. The method according to Item 4 wherein the solution contains at least one member selected from the group consisting of starch hydrolysates and reduced starch hydrolysates in a total concentration of 10 to 60 wt %.

Item 6. The method according to Item 4 wherein the drying surface has a temperature of 100° C. to 200° C.

Item 7. The method according to Item 5 wherein the drying surface has a temperature of 100° C. to 200° C.

Item 8. The method according to Item 4 wherein the solution is sprayed through a fluid nozzle.

Item 9. The method according to Item 5 wherein the solution is sprayed through a fluid nozzle.

Item 10. The method according to Item 6 wherein the solution is sprayed through a fluid nozzle.

Item 11. The method according to Item 7 wherein the solution is sprayed through a fluid nozzle.

Item 12. The method according to Item 8 wherein the fluid nozzle is a one-fluid nozzle or a two-fluid nozzle.

Item 13. The method according to Item 9 wherein the fluid nozzle is a one-fluid nozzle or a two-fluid nozzle.

Item 14. The method according to Item 10 wherein the fluid nozzle is a one-fluid nozzle or a two-fluid nozzle.

Item 15. The method according to Item 11 wherein the fluid nozzle is a one-fluid nozzle or a two-fluid nozzle.

(III) Method for Adsorbing an Oil by Using the Oil-Adsorbing Composition

Item 16. A method for adsorbing an oil, comprising a step of bringing the oil-adsorbing composition of Item 1 into contact with an oil or fat.

Item 17. A method for adsorbing an oil, comprising a step of bringing the oil-adsorbing composition of Item 2 into contact with an oil or fat.

Item 18. A method for adsorbing an oil, comprising a step of bringing the oil-adsorbing composition produced by the method of Item 3 into contact with an oil or fat.

Item 19. A method for adsorbing an oil, comprising a step of bringing the oil-adsorbing composition produced by the method of Item 4 into contact with an oil or fat.

Item 20. A method for adsorbing an oil, comprising a step of bringing the oil-adsorbing composition produced by the method of Item 5 into contact with an oil or fat.

Advantageous Effects of Invention

The oil-adsorbing composition according to the present invention has an excellent oil adsorption property and oil retention ability. Therefore, the oil-adsorbing composition of the present invention can adsorb and retain a larger amount of oil more efficiently than the oil-adsorbing composition produced by the conventional method (Patent Literature (PTL) 1). Furthermore, incineration of the powder after oil adsorption causes little environmental damage. Moreover, the oil-adsorbing composition of the present invention, which is produced by using a starch hydrolysate or a reduced starch hydrolysate as a starting material, can be applied to living organisms. More specifically, foods, drugs, cosmetics, detergents, clothing, etc., that contain the oil-adsorbing composition of the present invention have oil adsorption ability.

Further, an intermediate product, such as a porous film, is not produced by the production method of the present invention, thus with simplifying the production steps and facilitating the maintenance of the obtained oil-adsorbing composition. According to the production method of the present invention, a solution containing a starch hydrolysate or a reduced starch hydrolysate is sprayed, and the resulting droplets are dried and exfoliated. Therefore, less time is required to produce the oil-adsorbing composition, thus increasing the production efficiency. Further, the exposure time of a solution containing a starch hydrolysate and/or a reduced starch hydrolysate to high temperatures is shortened. This reduces the possibility of denaturation of heat-sensitive starch hydrolysate and reduced starch hydrolysate components. Further, the equipment required to carry out the present invention can be simplified and reduced in size, compared to conventional equipment, thus facilitating equipment management, equipment maintenance cost, and equipment cleaning.

DESCRIPTION OF EMBODIMENTS (Starch)

Figure 1:
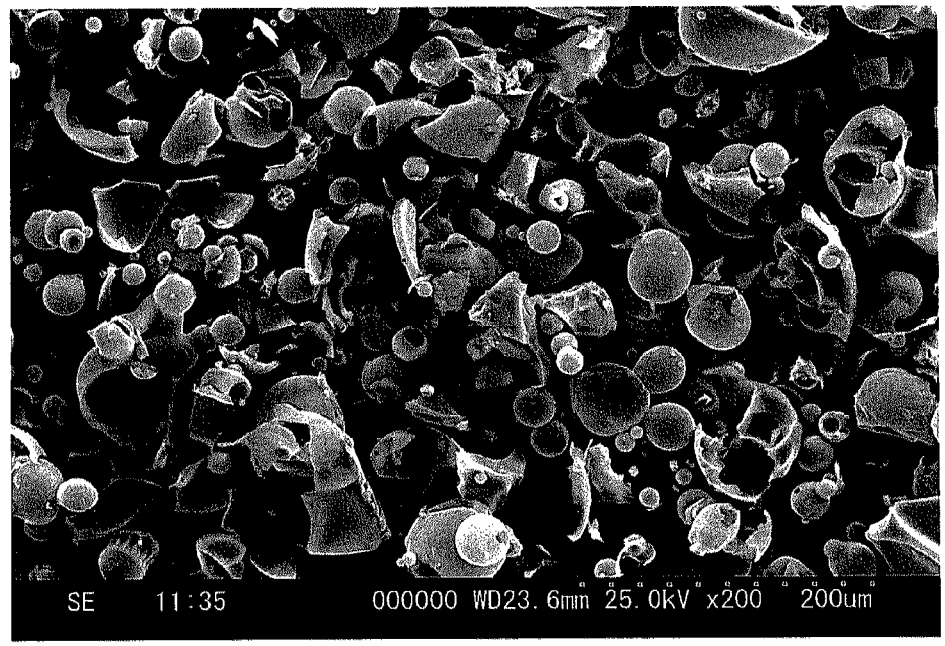
FIG. 1 shows an electron microscope photograph of the composition obtained in Example 1.

The oil-adsorbing composition of the present invention is produced by using a composition containing at least one member selected from the group consisting of starch hydrolysates and reduced starch hydrolysates. The starch as used herein includes, for example, natural starches such as tapioca starch, sago starch, potato starch, wheat starch, rice starch, sweet potato starch, corn starch, and waxy corn starch; and modified starches thereof (acetylated distarch phosphate, acetylated oxidized starch, acetylated distarch adipate, starch sodium octenylsuccinate, starch acetate, oxidized starch, hydroxypropylated distarch phosphate, hydroxypropyl starch, phosphorylated starch, distarch phosphate, and phosphated distarch phosphate).

(Starch Hydrolysate)

The starch hydrolysate as used herein is obtained by subjecting a starch as exemplified above to one or more hydrolysis treatments such as acidic decomposition, alkaline decomposition, enzymatic decomposition, and roasting. The starch hydrolysate may contain one hydrolysate, or a combination of two or more hydrolysates.

(Reduced Starch Hydrolysate)

The reduced starch hydrolysate as used herein is obtained by reducing a starch hydrolysate as exemplified above into a sugar alcohol. The reduced starch hydrolysate may contain one reduced starch hydrolysate, or a combination of two or more reduced starch hydrolysates.

(DE)

The starch hydrolysate used in the present invention preferably has a DE of 1 to 20, more preferably 6 to 16, and even more preferably 9 to 12. DE as used herein stands for Dextrose Equivalent; DE is an index value that describes the degree of degradation of a starch hydrolysate (saccharification rate). As shown in the formula below, the amount of reducing sugar in a sample is expressed as a glucose percentage, based on the solids content.

"DE" in the present description is a value represented by the formula:

$$[(\text{Mass of direct reducing sugar (expressed as glucose)})/(\text{Mass of solids content}) \times 100].$$

DE is an analytical value obtained by the Willstätter-Schudel method. The maximum of DE is 100. A DE of 100 means that the solids are entirely glucose. More specifically, complete degradation of a starch results in 100% glucose; in this case, the DE would be 100. The smaller the DE, the lower the degree of decomposition.

A starch hydrolysate with a DE value of less than 1 increases the viscosity of the solution, whereas a starch hydrolysate with a DE value of more than 20 increases the hygroscopicity, thus resulting in difficulty in drying the solution. Further, DE is related to the viscosity of starch hydrolysates. A starch hydrolysate with a higher DE tends to have a lower viscosity.

(Solution)

The above solution is produced by dissolving at least one member selected from starch hydrolysates and reduced starch hydrolysates as mentioned above in a solvent. The solvent as used herein is not particularly limited. Examples of usable solvents include water, hydrous alcohol, and the like. Water is preferable. The concentration of at least one member selected from the group consisting of starch hydrolysates and reduced starch hydrolysates dissolved in such a solvent is not particularly limited. The total concentration thereof in the solution is preferably 10 wt % to 60 wt %, more preferably 20 wt % to 55 wt %, and even more preferably 30 wt % to 50 wt %. The solution of a starch hydrolysate with a low DE tends to have a high viscosity. Therefore, when a starch hydrolysate with a low DE is used, a low concentration thereof in the solution is preferable to avoid an excessively high viscosity of the solution. For example, when a starch hydrolysate with a DE of 6 or less is used, its concentration in the solution is adjusted to less than 50 wt %. In addition, the solution may contain other components. Examples of other components include glycerol, oxidized starch, ethylene glycol, high molecular weight polysaccharides, flavoring agents, colorants, bases, inorganic and organic acids, high-sensitivity sweeteners, seasonings containing amino acids and proteolysates, and the like.

(Spraying)

The oil-adsorbing composition of the present invention is produced by spraying the solution and drying the resulting droplets. A fluid nozzle may be used to spray the solution.

The fluid nozzle as used herein is not particularly limited in configuration. For example, a one-fluid nozzle or a two-fluid nozzle can be used. The one-fluid nozzle may have a flat-type, a full cone-type, hollow cone-type, fine mist-type, or like configuration. The two-fluid nozzle may have a continuous spray-type, automatic gun-type, or like configuration. The material of the spray nozzle is not particularly limited; and may be, for example, SUS, brass, ceramics, various resins, plastics, etc.

The droplets are not particularly limited in size and shape. For example, when a one-fluid nozzle is used, the particle size of the droplets is determined according to the configuration of the spray nozzle, solution viscosity, flow rate, fluid pressure, etc. When a two-fluid nozzle is used, the particle size of the droplets is determined according to the configuration of the spray nozzle, solution viscosity, flow rate, and atomizing air pressure. For example, as the atomizing air pressure increases, the particle size of the obtained droplets is reduced. As the flow rate of the solution increases, the particle size of the droplets increases.

Whether a one-fluid or two-fluid nozzle is used, a nozzle having a flat-type configuration is preferably used for spraying. The amount of spray application is preferably 0.01 to 0.1 g/cm$^2$. When using a two-fluid nozzle, the atomizing air pressure is preferably 0.01 mhPa to 0.5 mhPa.

(Drying)

As a method for drying droplets, the solution is sprayed onto a drying surface to form droplets thereon. The drying surface may be any surface that can dry droplets. Preferably, the surface can heat or keep droplets warm. Examples of such drying surfaces include metallic plates, drum surfaces of drum dryers, etc. The metallic plate is not particularly limited in material, shape, and size. The drum dryer to be used is not particularly limited in configuration, and may be, for example, a single drier, a double drier, a twin drier, etc. When a drum dryer is used, dryer operating conditions are not particularly limited. The drying temperature and revolution speed can be suitably adjusted according to the starting materials used for producing the oil-adsorbing composition, and properties of the obtained oil-adsorbing composition, such as bulk specific gravity.

When the droplets are dried on a drying surface, the drying surface typically has a temperature of 100° C. to 200° C., preferably 120° C. to 200° C., and more preferably 150° C. to 180° C. Although the drying completion time can be suitably set, the drying time is preferably 4 to 10 seconds.

When the amount of droplets to be dried (the amount of solution sprayed onto the drying surface) is excessively large, droplets are contacted with each other, thus failing to provide a satisfactory dried material. On the other hand, an excessively small amount of droplets to be dried (amount of solution sprayed onto the drying surface) results in low productivity, which increases production cost. Therefore, the amount of solution sprayed is preferably controlled so as to maintain a constant amount of droplets to be dried.

(Oil-Adsorbing Composition)

As described above, the oil-adsorbing composition of the present invention is produced by drying a solution of a starch hydrolysate or a reduced starch hydrolysate in a droplet state, and exfoliating the droplets. Accordingly, the oil-adsorbing composition may comprise hollow spheres. The oil-adsorbing composition may further comprise, in addition to the hollow spheres, fragments thereof and/or strips formed by drying a solution of a starch hydrolysate or a reduced starch hydrolysate. This is because when a solution of a starch hydrolysate or a reduced starch hydrolysate is sprayed, not only are droplets dried to hollow spheres and fragments thereof, but splashes are also dried into strips. Observation through an electron microscope and analysis with a particle size distribution analyzer show that the oil-adsorbing composition preferably has a mean particle diameter of 120 µm or more, more preferably 140 µm or more, and most preferably 220 µm or more. The oil-adsorbing composition with a mean particle diameter of less than 120 µm tends to have a small volume and low oil adsorption ability. On the other hand, a larger mean particle diameter of the oil-adsorbing composition is expected to increase the amount of oil adsorbed; however, a mean particle diameter of about 2,000 µm or less is preferable. An oil-adsorbing composition with a mean particle diameter of more than about 3,000 µm is difficult to use. Further, because the oil-adsorbing composition applied to a drying surface in droplet form is boiled while maintaining the droplet state by the viscosity of the solution, steam is emitted from the solution, forming droplets having internal porosity. Thus, the oil-adsorbing composition is porous.

(Bulk Specific Gravity)

A feature of the oil-adsorbing composition is having a specific shape produced by its production method. Another feature of the composition is preferably having a bulk specific gravity of 6 cm$^3$/g or more, more preferably 6.8 cm$^3$/g or more, and even more preferably 7.5 cm$^3$/g or more. Although the upper limit of the bulk specific gravity is not particularly limited, it may typically be 15 cm$^3$/g or less.

The bulk specific gravity as referred to herein can be calculated by the following method. A 10 g equivalent of the obtained oil-adsorbing composition is gently poured into a graduated cylinder. From the scale of the cylinder, the volume (ml) of the composition is measured. After this operation is repeated 10 times, the average volume A (ml) is calculated from the measured volumes. The bulk specific gravity can be calculated from the following equation.

$$\text{Bulk specific gravity (cm}^3/\text{g)} = 0.1 \times A$$

(Oil)

The oil-adsorbing composition of the present invention is brought into contact with an oil to thereby adsorb the oil (oil adsorption ability) and retain the oil (oil retention ability). The oil as used herein includes, for example, vegetable oils, animal oils, mineral oils, crude oils, and like various oils; oils and fats, oily vitamins, high-sensitivity sweeteners, colorants, flavoring agents, and like alcoholic extracts; and oily substances extracted from animals, plants, and animal- or plant-related substances.

Examples of vegetable oils include shortening, margarine, salad oil, orange oil, soybean lecithin, flavoring agents, fragrant oils, and spicy oils, safflower oil, soybean oil, rapeseed oil, palm oil, palm kernel oil, cottonseed oil, coconut oil, rice bran oil, sesame oil, castor oil, linseed oil, olive oil, tung oil, camellia oil, peanut oil, kapok oil, cacao seed oil, wax, sunflower oil, corn oil, and like vegetable fats and oils. These fats and oils can be used singly, or in a combination of two or more.

It is generally preferable that the oil-adsorbing composition of the present invention has the following oil adsorption ability in a normal temperature condition: the composition can adsorb salad oil in an amount of 190 ml or more, and preferably 200 ml or more, per 100 g of the composition; the composition can adsorb orange oil in an amount of 200 ml or more, and preferably 250 ml or more, per 100 g of the composition; and the composition can adsorb lecithin in an amount of 125 ml or more, and preferably 155 ml of more, per 100 g of the composition.

Examples of animal oils include butter, margarine, refined oil, lard, beef tallow, sardine oil, herring oil, cuttlefish oil, saury oil, and like fish oils; liver oil, whale oil, beef tallow, butterfat, horse oil, lard, mutton tallow, and like animal or vegetable fats and oils. These fats and oils can be used singly, or in a combination of two or more.

Examples of mineral oils include various lubricating oils such as spindle oils, refrigerating machine oils, dynamo oils, turbine oils, machine oils, marine internal combustion engine lubricants, gasoline engine lubricants, diesel engine lubricants, cylinder oils, marine engine oils, gear oils, cutting oils, insulating oils, automatic transmission fluids, compressor oils, hydraulic oils, rolling oils, and the like.

Examples of other oils include crude oil, fuel oil, light oil, gasoline, various waste oils, and the like; for example, waste oils discharged from processed marine product factories, processed livestock product factories, metal rolling mills, metal processing plants, etc.

(Method of Use for Oil Adsorption)

The method of using the oil-adsorbing composition of the present invention can powder an oil or fat by physical adsorption without emulsification; and therefore does not comprise heat treatment, and thus does not cause thermal denaturation of the fat and oil component. Furthermore, the method, which enables powderization without emulsification, does not impair the natural functions of oils and fats. However, the purpose of use of the oil-adsorbing composition of the present invention and the method of using the composition are not limited to those mentioned above, and various other methods of use are also possible. The method of using the oil-adsorbing composition of the present invention comprises a step of bringing the oil-adsorbing composition into contact with an oil or fat. The manner of bringing the oil-adsorbing composition of the present invention into contact with an oil or fat includes for example, mixing the oil-adsorbing composition of the present invention with an oil or fat; sprinkling the oil-adsorbing composition of the present invention onto the surface of an oil or fat; and adding an oil or fat to a column packed with the oil-absorbing composition of the present invention. Thus, the manner is not particularly limited.

(Method of Use for Oil Release)

The oil-adsorbing composition of the present invention after adsorption of an oil can release the adsorbed oil when mixed with various types of solvents. The solvents as used herein are not particularly limited. Examples of usable solvents include water, hot water, soft drinks, alcoholic beverages, tea drinks, carbonated beverages, soups, and like drinkable foodstuffs; mince, leavening, rice cake dough, and like foods with water content; and acid solutions, alkali solutions, clay, ceramic starting materials, and like materials with water content. The method of using the oil-adsorbing composition of the present invention may be, for example, a method comprising heating and liquefying lard; uniformly mixing the oil-adsorbing composition with the liquid lard; powdering the mixture; and adding the resulting powder to a ramen soup powder, thus obviating the necessity of separately packaging the lard and soup. When the powdered lard co-packaged with the ramen soup powder is placed in hot water during cooking, the oil-adsorbing composition having an oil adsorbed thereon is dissolved, thereby causing the lard to float on the liquid surface of the ramen soup. The oil-adsorbing composition of the present invention after adsorption of an oil can release the adsorbed water when mixed with various types of solvents.

The following examples are presented to further describe the present invention. However, the present invention is not intended to be limited in scope by any of the following examples.

Example 1

(Solution Concentration-Bulk Specific Gravity)

A starch hydrolysate (a product of Matsutani Chemical Industry Co., Ltd.) (DE 12) was dissolved in water to prepare aqueous solutions of the starch hydrolysate in concentrations of 10 wt %, 20 wt %, 30 wt %, 40 wt %, 50 wt %, and 60 wt %. Each of the aqueous starch hydrolysate solutions thus prepared was sprayed onto the drum surface of a double drum dryer (internal steam pressure: 0.6 MhPa/cm$^3$) by a Spraying System Co. two-fluid nozzle (SUE15-SS) to a coating weight of 0.025 g/cm$^2$, and dried at a drum surface temperature of 155° C., an environmental temperature of 29° C., and a humidity of 60%. The resulting dried product was screened through a 20-mesh sieve. Subsequently, the bulk specific gravity (cm$^3$/g) of the oil-adsorbing compositions (Samples 1 to 6) prepared from the aqueous solutions of the starch hydrolysate in various concentrations was measured. Table 1 below shows the measurement results. The coating weight (g/cm$^2$) was determined as a coating amount per square meter from the amount of solution applied per unit time by calculating the area according to the following equation: Area=Number of revolutions of the double drum dryer per unit time×Outer circumference of the drum×Application width on the drum.

TABLE 1

| Sample No. | Concentration of the aqueous starch hydrolysate solution (wt %) | Bulk specific gravity (cm$^3$/g) |
|---|---|---|
| 1 | 10 | 6.0 |
| 2 | 20 | 7.5 |
| 3 | 30 | 8.0 |
| 4 | 40 | 9.9 |
| 5 | 50 | 11.0 |
| 6 | 60 | 6.8 |

The oil-adsorbing composition (Sample 1) produced using a 10 wt % aqueous starch hydrolysate solution had a bulk specific gravity of 6.0 cm$^3$/g. The bulk specific gravity of the oil-adsorbing compositions (Samples 1 to 5) produced using 10 wt % to 50 wt % aqueous starch hydrolysate solutions increased depending on an increase in the concentration of the aqueous starch hydrolysate solution. When a 50 wt % aqueous starch hydrolysate solution is used, the obtained oil-adsorbing composition (Sample 5) had a bulk specific gravity of 11.0 cm$^3$/g.

Comparative Example 1

A starch hydrolysate (a product of Matsutani Chemical Industry Co., Ltd.) (DE 12) was dissolved in water to prepare a 50 wt % aqueous starch hydrolysate solution. The aqueous starch hydrolysate solution was sprayed in a solution state on the drum surface of a double drum dryer (internal steam pressure: 0.6 MhPa/cm$^3$, revolution speed: 17 seconds/revolution, roll slit: 0.1 mm), and dried at a drum surface temperature of 155° C., an environmental temperature of 29° C., and a humidity of 60%. The resulting dried product was screened through a 20-mesh sieve. The dried material thus obtained was termed Comparative Example 1. The bulk specific gravity of Comparative Example 1 was 10.1 cm$^3$/g, which is smaller than the bulk specific gravity (11 cm$^3$/g) of the oil-adsorbing composition produced in Example 1 from an aqueous solution of the starch hydrolysate in the same concentration (50 wt %). This result indicates that when the same solution is used as a starting material, a dried material produced by the method of the present invention tends to have a bulk gravity larger than the dried material produced by the conventional technique.

Experiment Example 1

<Observation of Shape Difference with an Electron Microscope>

Figure 2:
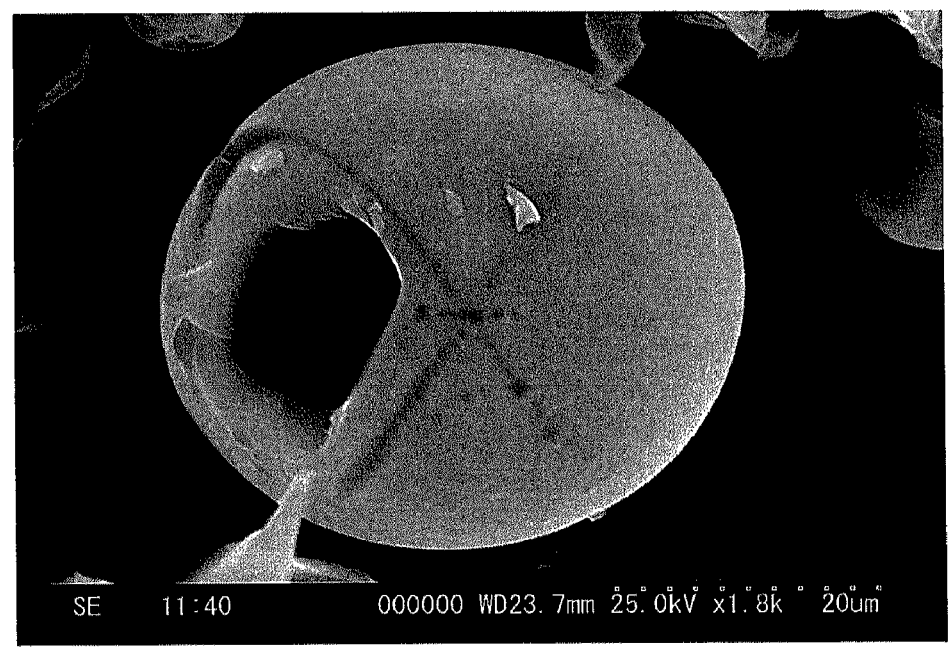
FIG. 2 shows an electron microscope photograph of one droplet of the composition obtained in Example 1.
Figure 3:
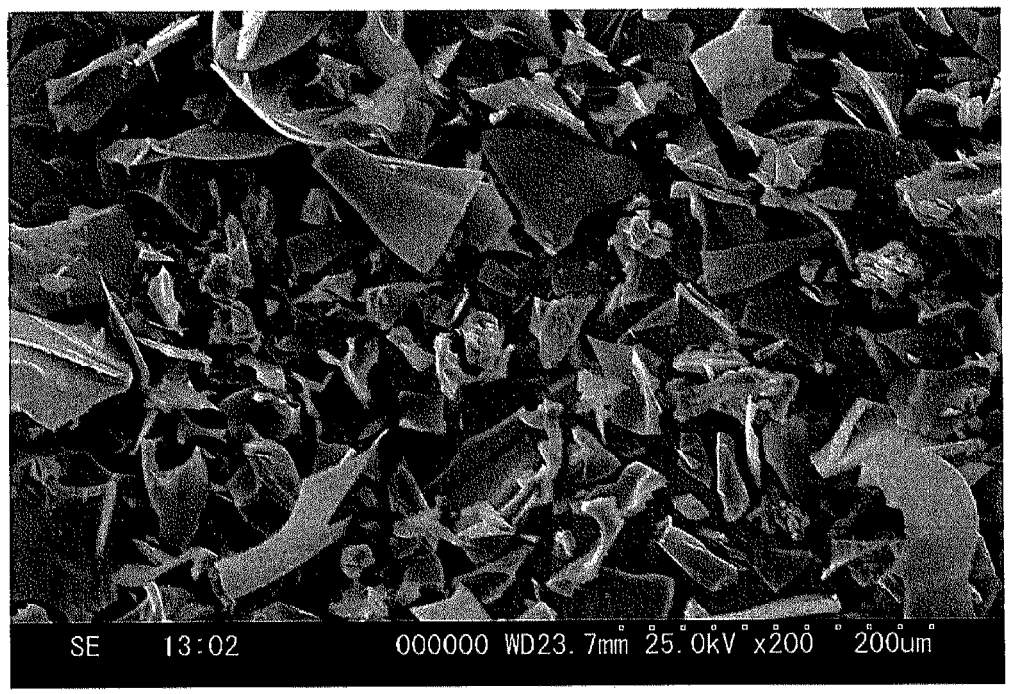
FIG. 3 shows an electron microscope photograph of the composition obtained in Comparative Example 1.

The shape of the dried material of Sample 5 (produced using a 50 wt % solution) in Example 1 and that of Comparative Example 1 were observed with an electron microscope. As shown in FIGS. 1 and 2, Sample 5 obtained in Example 1 contained hollow spheres and fragments thereof. In contrast, the composition obtained in Comparative Example 1 did not contain hollow spheres or fragments thereof, but instead contains many strips (FIG. 3). The compositions of Example 1 and Comparative Example 1 were both porous.

Experimental Example 2

<Measurement of the Particle Diameter with a Particle Size Distribution Analyzer>

The mean particle diameter of each sample obtained in Example 1 was determined by suspending each sample in ethanol, and measuring the mean particle diameter using a laser analysis/scattering/particle size/particle size distribution analyzer (MT-3300-II) produced by Nikkiso Co., Ltd. Table 2 shows the results.

TABLE 2

| Sample No. | Minimum particle diameter (μm) | Maximum particle diameter (μm) | Mean particle diameter (μm) |
| --- | --- | --- | --- |
| 1 | 16.0 | 383.0 | 120.7 |
| 2 | 15.3 | 542.9 | 140.2 |
| 3 | 16.8 | 777.0 | 229.0 |
| 4 | 16.3 | 798.0 | 251.0 |
| 5 | 14.3 | 995.6 | 249.3 |
| 6 | 15.5 | 402.0 | 190.3 |

Experimental Example 3

<Physical Durability Experiment>

The oil-adsorbing composition produced by the conventional technique had excellent physical durability. To compare the physical durability of the oil-adsorbing composition of the present invention with that of the conventional composition, their particle durability under stirring shear force was examined. For example, when air is suctioned from a packed sample, suction force is applied to each particle, and particles that can withstand the suction force can maintain their shape and size. Accordingly, bulk specific gravity of the sample before and after suction was measured. When the ratio of the bulk specific gravity after suction to that before suction is calculated as the residual bulk specific gravity after suction, the residual bulk specific gravity of each sample can be compared as an index of particle durability under stirring shear force. As a result, the durability of each sample to suction force, i.e., physical durability, can be compared and examined. Accordingly, a 1 kg equivalent of each sample was actually placed in a container (or a graduated cylinder), and suctioned twice with a low suction force using a vacuum cleaner "DC26" (product name) produced by Dyson. This operation was repeated 4 times, and the average residual bulk specific gravity was calculated from the bulk specific gravity difference before and after suction. Table 3 shows the residual bulk specific gravity of each sample after suction.

TABLE 3

|  | Residual bulk specific gravity after the first suction | Residual bulk specific gravity after the second suction |
| --- | --- | --- |
| Sample 5 of Example 1 | 53.8% | 35.9% |
| Comparative Example 1 | 53.3% | 41.5% |

The results show that there is no substantial difference between Sample 5 of Example 1 and that of Comparative Example 1 in the residual bulk specific gravity, both after the first suction and after the second suction. The results show that the physical durability of Sample 5 of Example 1 prepared as an oil-adsorbing composition of the present invention is as high as that of the composition of Comparative Example 1 produced by a conventional method.

Experimental Example 4

<Comparison of Oil Adsorption Property and Oil Retention Ability>

To compare oil adsorption properties and oil retention ability between Example 1 (Samples 2, 3, and 5) and Comparative Example 1, properties of each sample after oil adsorption and exudation of oil when the sample was sandwiched between filter paper were observed. More specifically, 10 g of each sample was placed in a beaker, and 13 g of salad oil (trade name: "Nissin Salad Oil", produced by The Nisshin OilliO Group, Ltd.) was slowly added dropwise with stirring (room temperature). The properties of each sample having oil adsorbed thereon, and exudation of oil to milk filter paper when the sample was sandwiched between the milk filter paper (trade name: "Milk Sediment Disc", produced by Advantec Co., Ltd.) and allowed to stand for 20 minutes were observed. Table 4 shows the results.

TABLE 4

|  | Properties | Exudation onto the filter paper |
| --- | --- | --- |
| Comparative Example 1 (Bulk specific gravity: 10.1 cm$^3$/g) | Powdery but slightly clumpy | Slight exudation |
| Sample 5 of Example 1 (Bulk specific gravity: 11.0 cm$^3$/g) | Powdery but slightly clumpy | No exudation |
| Sample 3 of Example 1 (Bulk specific gravity: 8.0 cm$^3$/g) | Clumpy impression stronger than Sample 5 of Example 1 | No exudation |

TABLE 4-continued

| | Properties | Exudation onto the filter paper |
|---|---|---|
| Sample 2 of Example 1 (Bulk specific gravity: 7.5 cm³/g) | Clumpy impression stronger than Sample 5 of Example 1 | Very slight exudation |

The observation results of the properties of each sample after oil adsorption shown in Table 4 indicate that Sample 5 (bulk specific gravity: 11.0 cm³/g) of Example 1 maintains a powder state as in Comparative Example 1 (bulk specific gravity: 10.1 cm³/g), and has not reached an oil adsorption saturated state. On the other hand, the results confirm that Sample 2 (bulk specific gravity 7.5 cm³/g) and Sample 3 (bulk specific gravity 8.0 cm³/g) of Example 1 do not maintain a powder state, and have reached a saturated state. Specifically, the results suggest that as the bulk specific gravity increases, oil adsorption ability increases.

Subsequently, the observation results of exudation onto filter paper confirm that Sample 5 (bulk specific gravity: 11.0 cm³/g) and Sample 3 (bulk specific gravity: 8.0 cm³/g) of Example 1 are oil-adsorbing compositions that adsorbed the largest amount of oil. Sample 2 (bulk specific gravity: 7.5 cm³/g) of Example 1 resulted in the slight exudation of oil onto filter paper, but the oil exudation amount was smaller than that of Comparative Example 1 (bulk specific gravity: 10.1 cm³/g). Specifically, the results confirmed that all of the samples obtained in Example 1 have high oil retention ability after oil adsorption, compared to that of the oil-adsorbing composition produced by the conventional method. This is probably due to the shape difference in the oil-adsorbing composition. Further, the oil exudation amount of Sample 2 was greater than that of Sample 3. This result suggests that when there is no difference in shape, as the bulk specific gravity increases, oil retention ability after oil adsorption increases.

Experimental Example 5

<Measurement of the Amount of Oil Adsorbed>

Using salad oil ("Nissin Salad Oil", produced by The Nisshin OilliO Group, Ltd.), orange oil (trade name: "Orange Oil", produced by Yamakei Sangyo Co., Ltd.), and soybean lecithin (trade name: "Soy Lecithin", produced by ADM Co.), the amount of oil adsorbed by the dried material of Example 1 and that of Comparative Example 1 was measured according to JIS K 5101 to compare their oil adsorption ability. More specifically, about 1 to 5 g of each sample was placed on the center portion of a measurement plate. An oil and fat was gradually added dropwise to the center of the sample from a burette in an amount of 4 or 5 drops at a time. Each time, the entirety was thoroughly kneaded with a spatula. Dropping and kneading were repeated until the entirety became a hard putty-like mass. Thereafter, with each drop, the entirety was kneaded. The moment when the mixture becomes spirally windable with the last drop added is defined as the terminal point. However, when it is impossible to spirally wind the mixture, the moment immediately before rapid softening occurs with one drop is defined as the terminal point. The total amount of oil and fat added dropwise is defined as the amount of oil absorbed (Table 5). Table 5 shows the total amount of oil and fat absorbed per 100 g of each sample.

TABLE 5

| | Salad oil (ml/100 g) | Orange oil (ml/100 g) | Soybean lecithin (ml/100 g) |
|---|---|---|---|
| Comparative Example 1 (Bulk specific gravity: 10.1 cm³/g) | 190 | 200 | 125 |
| Sample 5 of Example 1 (Bulk specific gravity: 11.0 cm³/g) | 235 | 300 | 180 |
| Sample 3 of Example 1 (Bulk specific gravity: 8.0 cm³/g) | 205 | 260 | 155 |
| Sample 2 of Example 1 (Bulk specific gravity: 7.5 cm³/g) | 205 | 250 | 160 |

Table 5 shows that with respect to any of salad oil, orange oil, and soybean lecithin, Samples 2, 3, and 5 of Example 1 have a higher oil absorption property than the composition of Comparative Example 1.

Example 2

(DE-Bulk Specific Gravity)

To Compare the Bulk Specific Gravity of Oil-Adsorbing compositions, which differs due to the DE difference between starch hydrolysates used as starting materials, starch hydrolysates (produced by Matsutani Chemical Industry Co., Ltd.) that differ in DE (DE: 6, 9, 12, and 16) were dissolved in water to prepare aqueous solutions of starch hydrolysates (starch hydrolysate concentrations: 30, 40, and 50 wt %). Further, to compare the bulk specific gravity which differs due to the difference between a starch hydrolysate and a reduced starch hydrolysate, a reduced starch hydrolysate with a DE of 16 (produced by Matsutani Chemical Industry Co., Ltd.) was dissolved in water, and aqueous solutions of the reduced starch hydrolysate (reduced starch hydrolysate concentrations: 30, 40, and 50 wt %) were prepared. Subsequently, each of the aqueous solutions was sprayed onto the drum surface of a double drum dryer (internal steam pressure: 0.6 MhPa/cm³, coating weight: 0.015 g/cm²) using a Spraying System Co. two-fluid nozzle ("SUE15-SS"), and dried at a drum surface temperature of 155° C., an environmental temperature of 29° C., and a humidity of 60%. The resulting dried product was screened with a 20-mesh sieve, and the bulk specific gravity of the thus-obtained oil-adsorbing composition was measured (Table 6).

TABLE 6

| | 30 wt % aqueous solution | 40 wt % aqueous solution | 50 wt % aqueous solution |
|---|---|---|---|
| DE6 | 13.0 | 14.0 | Non-sprayable |
| DE9 | 13.0 | 15.0 | 14.0 |
| DE12 | 12.0 | 13.0 | 15.0 |
| DE16 | 11.0 | 11.5 | 12.0 |
| Reduced DE16 product | 8.0 | 10.0 | 10.0 |

As a result, compositions with a bulk specific gravity of 6 ml/g or more were obtained in any case. When a starch hydrolysate with a low DE (decomposition degree of starch) is used, a dried material with a high bulk specific gravity was obtained. This is probably for the following reason. A lower DE results in a higher viscosity of the solution, which exhibits excellent shape retention when sprayed in droplet form, thus providing a dried material with a high bulk specific gravity. When a 50 wt % solution was prepared from a starch hydrolysate with a DE of 6, the solution was non-sprayable due to an excessively high viscosity. From the viewpoint of production efficiency, a solution of a starch hydrolysate with a DE of 12 preferably has a concentration of 50 wt %.

Example 3

(Ratio of Starch Hydrolysate to Starch)

Droplets of a solution containing a mixture of a starch and a starch hydrolysate as a solute were dried. The relationship between the ratio of the starch hydrolysate in the solute and the bulk specific gravity of the resulting oil-adsorbing composition was examined. An oxidized starch (manufactured by Matsutani Chemical Industry Co., Ltd.) was mixed with a starch hydrolysate (DE12) at an oxidized starch/starch hydrolysate mixing ratio by weight of 1:0, 1:1, 1:2, and 1:3, on a solids basis. Solutions containing each mixture in concentrations of 30 wt %, 40 wt %, and 50 wt %, on a solids basis, were prepared. Each of the thus-prepared solutions was sprayed onto the drum surface of a double drum dryer (internal steam pressure: 0.6 MhPa/cm$^3$, coating weight: 0.015 g/cm$^2$) using a Spraying System Co. two-fluid nozzle ("SUE15-SS"), and dried at a drum surface temperature of 155° C., an environmental temperature of 29° C., and a humidity of 60%. The resulting dried product was screened with a 20-mesh sieve, and the bulk specific gravity of the thus-obtained oil-adsorbing composition was measured. Table 7 shows the results.

TABLE 7

| | Unit: cm$^3$/g | | |
|---|---|---|---|
| | Solute concentration 30 wt % | Solute concentration 40 wt % | Solute concentration 50 wt % |
| Oxidized starch: starch hydrolysate = 1:0 | 4.5 | 5.0 | 5.5 |
| Oxidized starch: starch hydrolysate = 1:1 | 5.0 | 5.2 | 5.5 |
| Oxidized starch: starch hydrolysate = 1:2 | 5.5 | 6.0 | 6.3 |
| Oxidized starch: starch hydrolysate = 1:3 | 6.0 | 6.5 | 7.5 |

When the solute contained no starch hydrolysate, the obtained oil-adsorbing composition had a low bulk specific gravity. When the weight ratio of the oxidized starch to starch hydrolysate was 1:3, the obtained oil-adsorbing composition had a high bulk specific gravity, compared to the composition containing no starch hydrolysate. When the weight ratio of the oxidized starch to the starch hydrolysate was 1:3 (solute concentration: 50 wt %), the resulting oil-adsorbing composition exhibited the highest bulk specific gravity (7.5 cm$^3$/g). Specifically, as the ratio of the starch hydrolysate in the solute increased, the bulk specific gravity of the resulting oil-adsorbing composition increased.

INDUSTRIAL APPLICABILITY

The thus obtained oil-adsorbing composition of the present invention exhibits an excellent oil adsorption property, and high oil retention ability. Furthermore, because the composition is derived from natural ingredients, its disposal after oil adsorption is easy. Therefore, the composition is highly useful in such food industries as confectioneries, bakeries, frozen desserts, reconstituted milk, frozen foods, artificial meat, etc.; as well as in such pharmaceutical fields as drugs, cosmetics, etc.; and is also effective in the industrial and agricultural fields.

The invention claimed is:

1. An oil-adsorbing composition, comprising: hollow spheres containing at least one member selected from the group consisting of starch hydrolysates, and reduced starch hydrolysates, the hollow spheres being obtained by drying a solution in a droplet form, and exfoliating the resulting dried material,
    wherein said drying is performed by spraying droplets of said solution onto a drying surface and then heating the droplets,
    wherein the hollow spheres have a mean particle diameter of at least 120 μm and the bulk specific gravity of the composition is at least 6 cm3/q.

2. The oil-adsorbing composition according to claim 1, further comprising fragments of the hollow spheres.

3. The oil-adsorbing composition according to claim 1, wherein the hollow spheres have a mean particle diameter of at least 220 μm.

4. The oil-adsorbing composition according to claim 1, wherein the solution contains at least one member selected from the group consisting of starch hydrolysates and reduced starch hydrolysates in a total concentration of 10 to 60 wt %.

5. The oil-adsorbing composition according to claim 1, wherein the solution contains at least one member selected from the group consisting of starch hydrolysates and reduced starch hydrolysates in a total concentration of 30 to 50 wt %.

6. The oil-adsorbing composition according to claim 1, wherein the starch hydrolysates has a DE of 1 to 20.

7. The oil-adsorbing composition according to claim 1, wherein the starch hydrolysates has a DE of 9 to 12.

8. The oil-adsorbing composition according to claim 1, wherein the solution contains at least one member selected from the group consisting of glycerol, oxidized starch, ethylene glycol, high molecular weight polysaccharides, flavoring agents, colorants, bases, inorganic and organic acids, high-sensitivity sweeteners, and seasonings.

* * * * *